United States Patent [19]

Carnell et al.

[11] Patent Number: 4,865,826

[45] Date of Patent: Sep. 12, 1989

[54] DESULPHURIZATION

[75] Inventors: Peter J. H. Carnell, Stockton-on-Tees; Warwick Lywood, Yarm, both of England

[73] Assignee: Imperial Chemical Industries PLC, London, England

[21] Appl. No.: 101,000

[22] Filed: Sep. 24, 1987

Related U.S. Application Data

[63] Continuation-in-part of Ser. No. 386, Jan. 5, 1987, abandoned.

[30] Foreign Application Priority Data

Jan. 10, 1986 [GB] United Kingdom ............... 8600574
Oct. 1, 1986 [GB] United Kingdom ............... 8623571
May 7, 1987 [GB] United Kingdom ............... 8710804

[51] Int. Cl.$^4$ ............................................. C01B 17/04
[52] U.S. Cl. ............................. 423/230; 423/244; 502/34; 502/56; 55/73
[58] Field of Search ............... 502/56, 34, 517; 423/242, 230, 244 R; 55/73

[56] References Cited

U.S. PATENT DOCUMENTS

| 3,072,458 | 1/1963 | Page | 502/34 |
|---|---|---|---|
| 3,384,601 | 5/1968 | Price | 502/34 |
| 3,492,083 | 1/1970 | Lowicki | 502/56 |
| 4,283,212 | 8/1981 | Graham et al. | 502/34 |
| 4,427,642 | 1/1984 | Arashi et al. | 502/56 |
| 4,489,047 | 12/1984 | de Jorg et al. | 502/517 |
| 4,534,943 | 8/1985 | Novak et al. | 423/230 |
| 4,717,552 | 1/1988 | Carnell et al. | 423/230 |

FOREIGN PATENT DOCUMENTS 2180848 8/1987 United Kingdom ............... 423/244

*Primary Examiner*—Anthony McFarlane
*Attorney, Agent, or Firm*—Cushman, Darby & Cushman

[57] ABSTRACT

Desulphurization of a feedstock using a regenerable sorbent to give a desulphurized stream, regeneration of the sorbent by heating, feedstock, and during at least the initial part of the cooling, at least part of the effluent from the sorbent is contacted with a non-regenerable particulate sorbent. The desired desulphurized product comprises the effluent from the regenerable sorbent that has bypassed the particulate sorbent.

Preferably the heat for regeneration is obtained by heat exchange with the products of combustion of the sulphur laden regeneration fluid.

In an alternative process using a particulate sorbent for a "polishing" operation, the regenerable sorbent is replaced by a membrane separation unit giving a desulphurized stream and a sulphur laden stream, which is combusted to heat, by heat exchange, the desulphurized stream before it passes through the particulate sorbent.

9 Claims, 3 Drawing Sheets

DESULPHURIZATION

This application is a continuation-in-part of U.S. application Ser. No. 000,386, filed Jan. 5, 1989, now abandoned.

This invention relates to desulphurisation and in particular to the removal of sulphur compounds such as hydrogen sulphide from a liquid or gaseous feedstock stream, particularly hydrocarbon streams such as natural gas.

BACKGROUND OF THE INVENTION

Liquid or gaseous feedstock streams, particularly hydrocarbon streams such as natural gas often contain substantial amounts of sulphur compounds, for example, where the hydrocarbon is gaseous, in an excess of 50 ppm by volume expressed as equivalent hydrogen sulphide.

Before use it is generally desirable to reduce the sulphur compounds content of the feedstock to a low level, for example to below 10 ppm by volume.

One method of sulphur compound removal that could be employed is to sorb sulphur compounds from the stream by the use of a regenerable sorbent material such as a molecular sieve, active charcoal, or alumina. In this process the sorption stage is effected at a relatively low, e.g. ambient, temperature, and regeneration of the sorbent can be effected by contacting the regenerable sorbent with a suitable fluid, e.g. part of the feed or product, heated to an elevated temperature, generally in a direction counter-current to the direction of flow when on sorption duty. In such a process after the regeneration stage, there is normally a step wherein the regenerable sorbent is cooled to the sorption temperature, prior to the return of the regenerable sorbent to sorption duty. This cooling step is necessary since the regenerable sorbents are not particularly effective at elevated temperatures and so return of the regenerable sorbent, while still hot, to sorption duty would result in a significant break-through of sulphur compounds into the product while the regenerable sorbent is cooling. This cooling step can be effected by passing part of the product, or feed, at the normal sorption temperature through the regenerable sorbent. Where, as is normal, the regeneration fluid is part of the feed or product stream, the fluid employed for the regeneration (including cooling) stage represents a considerable proportion of the feed or product and has to be sent to waste, and so renders this type of process unattractive economically except in certain specialised cases.

Another method of sulphur compound removal that is commonly employed is to contact the feedstock stream with a bed of particles of a suitable particulate non-regenerable sorbent, such as zinc oxide. While such beds enable a product stream of low sulphur content to be produced, such particulate non-regenerable sorbents have only a limited capacity and so if large quantities of sulphur compounds have to be removed, the beds of particulate non-regenerable sorbents need frequent replenishment.

SUMMARY OF THE INVENTION

We have devised a particularly effective process using a combination of the above methods.

Accordingly the present invention provides a process for the production of a desulphurised product stream from a sulphur compound laden feedstock stream comprising
  (a) contacting said feedstock stream with a regenerable sorbent at a first temperature, said sorbent being effective at said first temperature to sorb sulphur compounds from said feedstock stream,
    thereby providing a first effluent stream of reduced sulphur content;
  (b) regenerating said regenerable sorbent by heating said regenerable sorbent to a second temperature at which sulphur compounds are desorbed from said regenerable sorbent, said heating being effected by contacting said regenerable sorbent with a stream of a heated regeneration fluid,
    thereby producing a second effluent stream of sulphur compound laden regeneration fluid;
  (c) after regeneration of said regenerable sorbent by said heating, cooling said regenerable sorbent to said first temperature by contacting said regenerable sorbent with a stream of said feedstock,
    thereby producing a third effluent stream; and
  (d) passing at least part of said third effluent stream during at least the initial part of said cooling, and, optionally, at least part of said first effluent stream, through a bed of a particulate non-regenerable sorbent effective to sorb sulphur compounds,
whereby the effluent from said bed of particulate non-regenerable sorbent, together with any of said first and third effluent streams that has bypassed the particulate non-regenerable sorbent bed, constitutes the desulphurised product stream.

In a preferred form of the invention, where the regenerable sorbent is in the form of sorbent beds, and where it is desirable to maintain continuous production of a desulphurised product stream, two or more beds of regenerable sorbent are provided in parallel, such that whilst one or more of the regenerable sorbent beds is regenerating, another receives the sulphur compound laden feedstock stream, and to produce either a first effluent stream with a sulphur content consistent with the desired product specification, or a first effluent stream that requires further "polishing" by contacting with the bed of particulate non-regenerable sorbent.

In one form of the invention, where the regenerable sorbent is able to reduce the sulphur content of the feedstock down to the desired level during the normal sorption stage, i.e. while the regenerable sorbent is at the first temperature, the particulate non-regenerable sorbent bed may be employed to treat only the third effluent stream, i.e. the effluent from the regenerable sorbent while the latter is cooling to, or approaching, the first temperature. In this case it will be appreciated that it may not be necessary, in order to meet the product specification, that the third effluent stream is passed through the particulate non-regenerable sorbent during the whole of the cooling step: thus passage of the third effluent through the particulate non-regenerable sorbent bed may only be necessary until the regenerable sorbent has cooled from the second, ie regeneration, temperature to a temperature intermediate the first and second temperatures and at which the regenerable sorbent is able to effect sufficient sulphur compound removal to meet the product specification.

Alternatively, the particulate non-regenerable sorbent bed may also be used to treat some or all of the first effluent stream, i.e. the effluent stream from the regenerable sorbent during part or all of the normal sorption stage. In this way where beds of regenerable sorbent are employed, it may be possible to increase the time that the bed of regenerable sorbent is on sorption duty since it then not necessary to terminate the sorption stage before significant "breakthrough" of sulphur into the first effluent stream occurs. Further, it may be desirable to provide a controlled bypass so that part of the first effluent stream passes through the particulate non-regenerable sorbent while the remainder bypasses the particulate non-regenerable sorbent bed. Similarly there may be a controlled bypass by the third effluent stream. The proportion of the first and/or third effluent streams that bypasses the particulate non-regenerable sorbent bed is controlled so that the product stream has a sulphur content consistent with the desired product specification.

In a prefered form of the invention, where the sulphur removal process is continuous, and a regenerable sorbent provides a "coarse" sulphur removal effect, thereby generating a first effluent stream that is required to be "polished" by contacting of said first effluent stream with particulate non-regenerable sorbent, and where the fluid used to regenerate the regenerable sorbent is combustible, after use for said regeneration the resultant sulphur compound laden regeneration fluid, i.e. the second effluent stream, is combusted, and heat is recovered from the combustion products thereof by means of indirect heat exchange with said first effluent stream, prior to the contacting of said first effluent stream with said particulate non-regenerable sorbent.

Since, in this mode of operation, where a regenerable sorbent provides a "coarse" sulphur removal effect, thereby generating a first effluent stream that is required to be "polished" by contacting of said first effluent stream with particulate non-regenerable sorbent, complete regeneration of the regenerable adsorbent is not necessary, it is possible to use the sulphur-containing feedstock as the regeneration fluid. However it is generally convenient to use part of the first effluent stream or part of the product stream as the regeneration fluid.

In a preferred form of the invention, where the regeneration fluid is combustible, after use for said regeneration, the resultant sulphur laden regeneration fluid, i.e. the second effluent stream, is combusted and heat is recovered from the combustion products thereof by means of indirect heat exchange to heat the regeneration fluid to said second temperature. In this case it is preferred that the regeneration fluid flow is continuous.

The combustion, and recovery of heat from the combustion products of a sulphur compound laden stream is also of utility in a process wherein, instead of employing a regenerable sorbent, the sulphur compound laden feedstock is subjected to a separation technique such as membrane separation to separate the feedstock into a partially desulphurised stream and a sulphur laden stream. The recovered heat can be used to heat the partially desulphurised fluid stream prior to contacting some or all of the partially desulphurised fluid stream with a particulate non-regenerable sorbent effecting a "polishing" treatment.

Accordingly the invention further provides a process for the production of a desulphurised product stream from a combustible, sulphur-compound laden, feedstock stream comprising (a) subjecting said feedstock stream to a sulphur removal treatment producing a partially desulphurised first effluent stream and a combustible, sulphur-compound laden, second effluent stream;

(b) combusting said second effluent stream and recovering heat from the combustion products thereof by indirect heat exchange with at least part of said first effluent stream to heat the latter; and (c) contacting the heated first effluent stream with a particulate non-regenerable sorbent effective to sorb sulphur compounds;

whereby the effluent from said bed of particulate non-regenerable sorbent, together with any of said first effluent stream that has bypassed the particulate non-regenerable sorbent bed, constitutes the desulphurised product stream.

It will be appreciated that such a sulphur removal treatment includes treatment of the feedstock with a regenerable sorbent as aforesaid, the sulphur compound laden regeneration fluid constituting the second effluent stream as aforesaid.

BRIEF DESCRIPTION OF THE DRAWINGS

Three embodiments of the invention are described with reference to the accompanying drawings wherein.

DESCRIPTION OF THE PREFERRED EMBODIMENT

Figure 1:
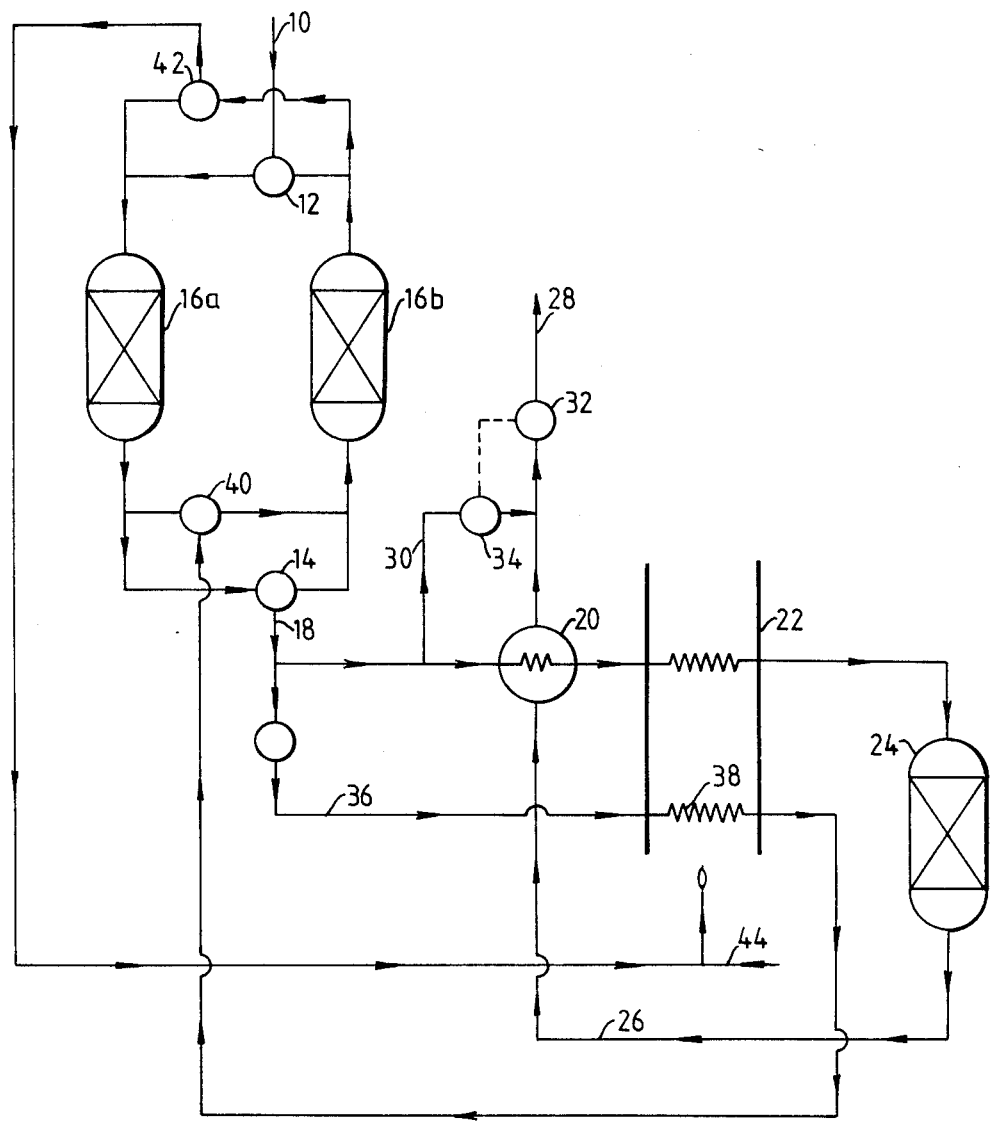
FIG. 1 is a flow sheet of a first embodiment wherein the regenerable sorbent is a molecular sieve and a single bed of particulate non-regenerable sorbent is employed.

In the system depicted in FIG. 1 the inlet feedstock stream, for example natural gas containing 100 ppm by volume of hydrogen sulphide, is fed via line 10 and valve 12 through a first molecular sieve bed 16a wherein the bulk of the hydrogen sulphide is sorbed by the molecular sieve. The resulting partially purified stream 18 is then fed from value 14 through a heat exchanger 20, and a fired heater 22 and then through a bed 24 of a particulate non-regenerable sorbent, for example zinc oxide. The purified gas stream 26 leaving bed 24 is then fed, via heat exchanger 20, to a product line 28. A bypass stream 30, taken from stream 18 and bypassing heat exchanger 20, heater 22, and bed 24, is reunited with the product line 28. The extent of bypass is controlled by a sensor 32 operating a valve 34 in the bypass line so that the product stream meets the desired sulphur content specification, for example 1 to 4 ppm by volume. While the first molecular sieve bed 16a is on sorption duty, a second molecular sieve bed 16b is undergoing regeneration by passing part of the partially purified gas stream 18, via valve 15 and line 36, through a heat exchanger 38 heated by the fired heater 22 and then, via valve 40 through the bed 16b and value 42. The gas swept out of the molecular sieve bed 16b is combusted with air supplied via line 44 and heats heater 22. The resulting flue gas may be treated in a sulphur recovery unit (not shown). The purpose of heater 22, and the feed/effluent heat exchanger 20, is to raise the temperature of the partially purified gas stream entering the particulate non-regenerable sorbent bed 24 to a temperature, for example 150° to 400° C., at which the latter has an improved sulphur capacity, as well as heating the regeneration gas to the desired regeneration temperature.

When bed 16b has been regenerated, valves 12, 14, 40, and 42 are switched to place bed 16b on sorption duty and to effect regeneration of bed 16a. Initially the newly regenerated sorbent bed is hot as a result of the passage therethrough of the hot regeneration gas. Upon switching of the feed from bed 16a to 16b, the feed cools bed 16b. However while bed 16b is still hot its sulphur adsorption capacity is limited, but any excess of sulphur "breaking through" into the stream 18 will be sorbed by the particulate non-regenerable sorbent bed 24. As bed 16b cools its ability to sorb sulphur increases and so, if desired, the proportion of stream 18 bypassing the particulate non-regenerable sorbent bed 24 via bypass 30 can be increased.

It will be appreciated that the stream 36 could be taken from product line 28 instead of from stream 18. However the use of part of the product stream as regeneration fluid is less preferred as this means that some sulphur is needlessly sorbed by the particulate non-regenerable sorbent. Alternatively stream 36 could be taken from the feed line 10 instead of from the partially purified gas stream 18.

Figure 2:
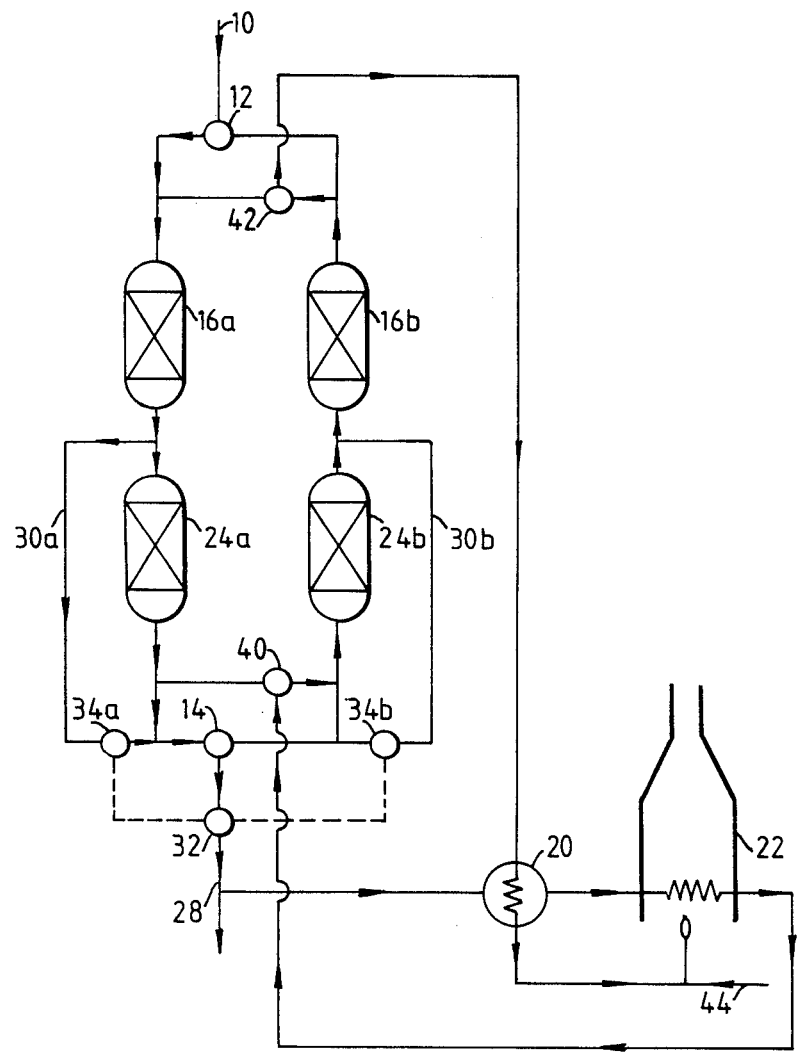
FIG. 2 is a flowsheet of a second embodiment wherein the regenerable sorbent is a molecular sieve but two beds of particulate non-regenerable sorbent are employed and the heated regeneration fluid is also passed through one of the particulate non-regenerable sorbent beds during regeneration of the molecular sieve.

In the embodiment of FIG. 2 a bed of particulate non-regenerable sorbent is disposed in series with each molecular sieve bed and during the sweetening, i.e. sulphur-compound removal, mode, the gas stream passing through the particulate non-regenerable sorbent bed is not heated. Thus, as in the embodiment of FIG. 1, the inlet gas is fed, via valve 12, to a molecular sieve bed 16a on sorption duty and then through a particulate non-regenerable sorbent bed 24a, which may be provided, as described above, with a bypass 30a. While bed 16a is on sorption duty, molecular sieve bed 16b is undergoing regeneration by passing part of the product gas stream (or part of the stream bypassing particulate non-regenerable sorbent bed 24a) through heat exchanger 20 and a fired heater 22 and then countercurrently (compared to normal sorption duty) through particulate non-regenerable sorbent bed 24b and its associated molecular sieve bed 16b. The gas leaving the molecular sieve bed 16b is then passed through the heat exchanger 20 and combusted as the fuel in fired heater 22. When molecular sieve bed 16b has been regenerated, valves 12, 14, 40, and 42 are switched to place bed 16b on sorption duty and to effect regeneration of bed 16a. As described in EP-A-230146, the intermittent heating of the particulate non-regenerable sorbent beds 24a 24b caused by the passage of heated gas therethrough during the regeneration of the associated molecular sieve bed has the effect of significantly increasing the sorption capacity of the particulate non-regenerable sorbent bed.

Figure 3:
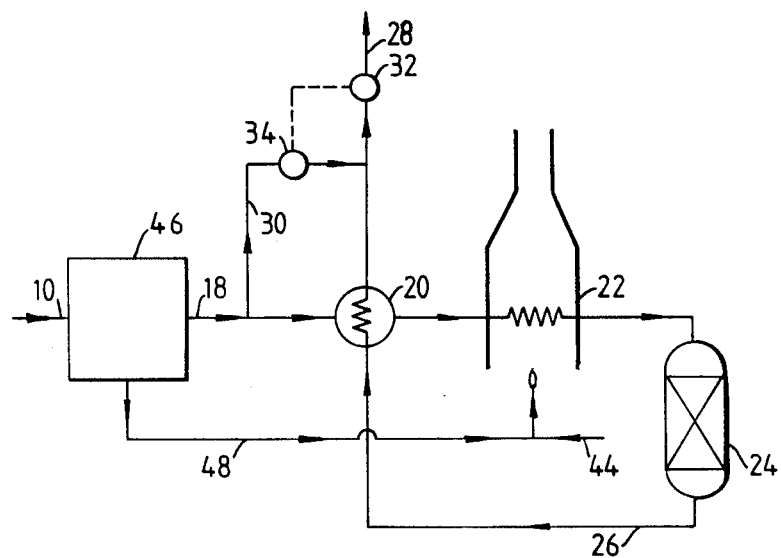
FIG. 3 is a flow sheet of a third embodiment wherein a partially desulphurised stream and a sulphur compound laden stream are obtained by means of a membrane system.

In the system depicted in FIG. 3 the inlet feedstock stream, for example natural gas containing 100 ppm by volume of hydrogen sulphide, is fed via line 10 to a membrane separation unit 46 wherein it is separated into a stream 18 of natural gas of reduced sulphur content, for example 10 ppm by volume and a stream 48 of gas containing the bulk of the hydrogen sulphide. The reduced sulphur content stream 18 is passed, as in the embodiment of FIG. 1, through a heat exchanger 20, and a fired heater 22 and then through a bed 24 of a particulate sorbent, for example zinc oxide. The purified gas stream 26 leaving bed 24 is then fed, via heat exchanger 20, to a product line 28. A bypass stream 30, taken from stream 18 and bypassing heat exchanger 20, heater 22, and bed 24, is reunited with the product line 28. The extent of bypass is controlled by a sensor 32 operating a valve 34 in the bypass line so that the product stream meets the desired sulphur content specification, for example 1 to 4 ppm by volume. Some or all of the stream 48 of natural gas loaded with the hydrogen sulphide separated in the membrane unit 46 is combusted with air supplied via line 44 and heats heater 22. The resulting flue gas may be treated in a sulphur recovery unit (not shown). The purpose of heater 22, and the feed/effluent heat exchanger 20, is to raise the temperature of the partially purified gas stream entering the particulate non-regenerable sorbent bed 24 to a temperature, for example 150° to 400° C., at which the latter has an improved sulphur capacity.

The inlet feedstock stream typically contains hydrocarbons up to those containing six carbon atoms. Usually it will contain, in addition to methane, one or more of ethane, propane, propene, butanes, and butenes. The invention is also of utility with other feedstocks, for example naphtha, carbon dioxide, refinery off gas, or the product of fractionating a gas mixture produced by cracking or hydrocracking a normally liquid hydrocarbon feedstock, or the gaseous by-product of a zeolite-catalysed conversion of a feedstock such as methanol to gasoline.

The composition of the raw gas, where the latter is a natural or oilfield associated gas, expressed by volume, is typically

| ethane | 2 to 20% |
| propane plus propene | 1 to 10% |
| butanes plus butenes | 0.5 to 5% |
| higher hydrocarbons | 0.2 to 2% |
| carbon dioxide | 0 to 20% |
| nitrogen | 0 to 20% |
| water | up to saturation |
| methane | balance. |

The sulphur compounds initially present in the feedstock stream usually include hydrogen sulphide and/or carbonyl sulphide, and possibly carbon disulphide, methyl mercaptan, diethyl sulphide, and/or tetrahydrothiophene. The total initial concentration of sulphur compounds, expressed as sulphur equivalent hydrogen sulphide, is typically in the range 10 to 1000 ppm by volume of the feedstock when the latter is in the gaseous phase. The sorption can be conducted so that a substantial proportion, e.g. over 75% by volume of the sulphur content of the feedstock stream can be removed. Typically the sulphur compounds content of the product is under 10, for example under 5, ppm by volume, expressed as above, but this is a matter of design, depending on the user's requirements.

In the process of the invention the temperature of the feedstock is typically in the range −10° to +50° C. Where the feedstock is heated prior to passage through the particulate non-regenerable sorbent bed, e.g. as in the first and third embodiments described above, the heating step is preferably conducted so as to increase the temperature to at least 50° C., and preferably to within the range 80° to 200° C.

It is preferred that, as in the embodiments described above, the heating of the stream passing through the particulate non-regenerable sorbent bed by heat exchange with the combustion products is effected after feed/effluent heat exchange, so that the temperature difference in the latter heat exchange is maximised.

Where the temperature of the gas stream passing through the bed of particulate non-regenerable sorbent is intermittently increased, as described in the embodiment of FIG. 2, it is preferred that the degree of heating is sufficient to increase the temperature of the non regenerable sorbent bed by at least 50° C., and in particular to a temperature in the range 150° to 350° C. as such intermittent heating has the effect of increasing the sorption capacity of the bed as described in EP-A-230146.

The particulate non-regenerable sorbent material preferably comprises at least 60, especially at least 80, % by weight of zinc oxide, calculated on the constituents of the particulate non-regenerable sorbent material non-volatile at 900° C. As used in the process the zinc oxide may be, at least initially, wholly or partly hydrated or in the form of a salt of a weak acid, e.g. a carbonate.

The particulate non-regenerable sorbent material is preferably in the form of porous agglomerates, as may be made, for example, by mixing a finely divided zinc oxide composition with a cement binder and a little water, insufficient to give a slurry, and then granulated or extruded. In order to aid access of the heated gas stream into the particles, the latter may be provided in the form of extruded pellets having a plurality of through passages. Typically the BET surface area of the particles is at least 20, preferably in the range 50 to 200, $m^2.g^{-1}$, and the pore volume of the particles is preferably at least 0.2 $cm^3.g^{-1}$.

Since the sorption efficiency and hence the life of a zinc oxide particulate bed depends on the rate of diffusion of the zinc sulphide formed by reaction of the zinc oxide with the sulphur compounds towards the interior of the particle, particularly at low sorption temperatures, it is preferable to employ zinc oxide particles having a high pore volume, above 0.2 $cm^3.g^{-1}$ and high surface area, above 50 $m^2.g^{-1}$. Thus while zinc oxide particles having a lower pore volume and a surface area of the order of 25 to 30 $m^2.g^{-1}$ can be employed, the bed life at low sorption temperatures is relatively low, necessitating the use of large bed volumes to avoid premature break-through of the sulphur compounds into the product stream. By using a bed of particles of pore volume above, for example, 0.25 $cm^3.g^{-1}$ and surface area above, for example, 70 $m^2.g^{-1}$, the bed volume can be markedly reduced, e.g. to about one third of that required with particles of low pore volume and surface area 25 to 30 $m^2.g^{-1}$. The particles employed thus preferably have a surface area above 50, particularly above 70, $m^2.g^{-1}$ and a pore volume above 0.25 $cm^3.g^{-1}$.

Preferred particulate non-regenerable sorbent materials for the process have a hydrogen sulphide sorption capacity of at least 20, especially at least 25, % of the theoretical, at a temperature of 25° C., as determined in a standard test in which a mixture of hydrogen sulphide (2000 ppm by volume), carbon dioxide (4% by volume), and methane (balance) is passed through a bed of the particles at atmospheric pressure and a space velocity of 700 $h^{-1}$ using a bed of circular cross section having a length to diameter ratio of 5.

A particularly suitable particulate non-regenerable zinc oxide material is that sold by Imperial Chemical Industries plc as "Catalyst 75-1". These particles are granules typically having a surface area of the order of 80 $m^2.g^{-1}$ and a pore volume of about 0.3 $cm^3.g^{-1}$, and an sorption capacity of about 27% of theoretical when measured by the above procedure.

Alternatively the particulate non-regenerable sorbent may comprise agglomerates of particles of an intimate mixture of oxides, hydroxides, carbonates and/or basic carbonates of copper, and zinc and/or at least one element such as aluminum as described in our copending European Patent Application 87303155.3.

Instead of using a bed, or beds, of an adsorbent such as a molecular sieve as the regenerable sorbent for the coarse sulphur removal stage, a regenerable liquid sorbent may be employed. By provision of a suitable circulatory system for the sorbent liquid continuous production of the required desulphurised product and continuous regeneration of said liquid sorbent may be effected.

In any of the above embodiments the desulphurised stream may be dried by means of a further molecular sieve downstream of the particulate sorbent bed. This molecular sieve may be regenerated by means of a heated stream, e.g. part of the product stream that has been passed through a heat exchanger heated by the combustion products.

As an example a typical molecular sieve system, having no particulate non-regenerable sorbent bed, for sorbing hydrogen sulphide from natural gas containing about 100 ppm and giving a product gas containing 1 ppm hydrogen sulphide, would require an sorption stage, with the feedstock at ambient temperature, of 8 hours, regeneration by passing gas heated to 280° C. through the bed in a counter-current direction for 4 hours followed by cooling by passing feed, or product, gas through the bed for 4 hours to cool the bed down to the normal sorption temperature. The amount of gas required for the regeneration and cooling is about 12% of the total product flow.

In accordance with the invention using an arrangement as shown in FIG. 1 using a bed of ICI "Catalyst 75-1" as the particulate non-regenerable sorbent, the sorption stage time can be increased to 8.5 hours since the hydrogen sulphide level of the gas leaving the regenerable sorbent bed during the sorption stage can be allowed to increase to above the 1 ppm specification, to for example 5 ppm. Regeneration, using feed heated to 280° C., could be effected for only 2 hours at a flow rate of 12% of the product flow, or preferably for the whole of the sorption time, ie 8.5 hours, at a rate of about 2.8% of the product flow.

We claim:

1. A process for the production of a desulphurised product stream from a sulphur compound laden feedstock stream comprising
    (a) contacting said feedstock stream with a regenerable sorbent at a first temperature, said sorbent being effective at said first temperature to sorb sulphur compounds from said feedstock stream,
       thereby providing a first effluent stream of reduced sulphur content which is discharged into a product stream;
    (b) regenerating said regenerable sorbent by heating said regenerable sorbent to a second temperature at which sulphur compounds are desorbed from said regenerable sorbent, said heating being effected by contacting said regenerable sorbent with a stream of a heated regeneration fluid,
       thereby producing a second effluent stream of sulphur compound laden regeneration fluid;

(c) after regeneration of said regenerable sorbent by said heating, cooling said regenerable sorbent to said first temperature by contacting said regenerable sorbent with a stream of said feedstock, thereby producing a third effluent stream which is discharged into said product stream; and (d) during at least the initial part of said cooling of said regenerable sorbent, passing at least part of said third effluent stream through a bed of a particulate non-regenerable sorbent effective to sorb sulphur compounds before discharge thereof into said product stream.

2. A process according to claim 1 wherein the second effluent stream is combustible, and combusting said second effluent stream and recovering heat from the combustion products thereof by indirect heat exchange with at least one stream selected from (i) at least part of the regeneration fluid prior to contacting said regeneration fluid with the regenerable sorbent; and (ii) at least part of the effluent stream that is contacted with the particulate non-regenerable sorbent, prior to contact thereof with the particulate non-regenerable sorbent.

3. A process according to claim 1 wherein the heated regeneration fluid comprises a heated portion of the first effluent stream.

4. A process as claimed in claim 1 wherein said particulate non-regenerable sorbent comprises agglomerates having a surface area of at least 50 $m^2.g^{-1}$ and a pore volume of at least 0.25 $cm^3.g^{-1}$, said agglomerates comprising at least 60% by weight zinc oxide, as calculated on the basis of the sorbent material which is non-volatile at 900° C.

5. A process as claimed in claim 1 wherein at least a first and second bed of regenerable sorbent are used, and the feedstock is fed to said first bed during said contacting step (a), and prior to regenerating said first bed during said regenerating step (b), the feed of said feedstock stream is switched from said first bed to said second bed whereby sulphur compounds are sorbed from said feedstock stream by said second bed of regenerable sorbent during the regeneration of the first bed, thereby providing a continuous flow of said first effluent.

6. A process as claimed in 5 wherein the heated regenerating fluid is passed through the bed of particulate non-regenerable sorbent prior to said regenerating fluid contacting the regenerable sorbent.

7. A process as claimed in claim 1 wherein at least one bed of regenerable sorbent is used through which said feedstock is passed in a first direction during said contacting step (a), and, in the regeneration step (b), the regenerating fluid is contacted with the regenerable sorbent by passing said regenerating fluid through the bed undergoing regeneration in a direction counter to said first direction.

8. A process for the production of a desulphurised product stream from a combustible, sulphur-compound laden, feedstock stream comprising (a) subjecting said feedstock stream to a sulphur removal treatment producing a partially desulphurised first effluent stream and a combustible, sulphur-compound laden, second effluent stream;

(b) discharging said first effluent stream into a desulphurised product stream;

(c) combusting said second effluent stream and recovering heat from the combustion products thereof by indirect heat exchange with at least part of said first effluent stream to form a heated stream;

(d) contacting the heated stream with a particulate non-regenerable sorbent effective to sorb sulphur compounds; and thereafter (e) discharging said heated stream into said desulphurised product stream.

9. A process for the production of a desulphurised product stream from a sulphur compound laden feedstock stream comprising (a) contacting said feedstock stream with a regenerable sorbent at a first temperature, said sorbent being effective at said first temperature to sorb sulphur compounds from said feedstock stream,
thereby providing a first effluent stream of reduced sulphur content which is discharged into a product stream;

(b) regenerating said regenerable sorbent by heating said regenerable sorbent to a second temperature at which sulphur compounds are desorbed from said regenerable sorbent, said heating being effected by contacting said regenerable sorbent with a stream of a heated combustible regeneration fluid,
thereby producing a combustible second effluent stream of sulphur compound laden regeneration fluid;

(c) after regeneration of said regenerable sorbent by said heating, cooling said regenerable sorbent to said first temperature by contacting said regenerable sorbent with a stream of said feedstock,
thereby producing a third effluent stream which is discharged into said product stream;

(d) passing, during at least the initial part of said cooling of said regenerble sorbent, at least a part of said third effluent streams through a bed of a particulate non-regenerable sorbent effective to sorb sulphur compounds before discharge thereof into said product stream and;

(e) combusting said second effluent stream and recovering heat from the combustion products by indirect heat exchange with at least one stream selected from (i) at least part of the regeneration fluid prior to contacting said regeneration fluid with the regenerable sorbent; and (ii) said at least part of said third effluent stream prior to passage thereof through said bed of particulate non-regenerable sorbent.

* * * * *